United States Patent [19]

Hitomi et al.

[11] Patent Number: 5,344,770
[45] Date of Patent: Sep. 6, 1994

[54] BACILLUS SP. FERM BP-3376 AND A METHOD FOR ITS USE TO PRODUCE AN ALKALINE PROTEINASE K-16

[75] Inventors: Jun Hitomi, Tochigi; Shigehito Adachi, Utsunomiya; Yoshihiro Hakamada; Mikio Takaiwa, both of Tochigi; Tadashi Yoshimatsu; Yōko Watanabe, both of Utsunomiya; Tohru Kobayashi, Tochigi; Shuji Kawai; Susumu Ito, both of Utsunomiya, all of Japan

[73] Assignee: Kao Corporation, Tokyo, Japan

[21] Appl. No.: 141,019

[22] Filed: Oct. 26, 1993

Related U.S. Application Data

[62] Division of Ser. No. 816,243, Jan. 3, 1992, Pat. No. 5,296,367.

[30] Foreign Application Priority Data

| Jan. 17, 1991 | [JP] | Japan | 3-17065 |
| Jan. 17, 1991 | [JP] | Japan | 3-17066 |
| Feb. 27, 1991 | [JP] | Japan | 3-33116 |
| Feb. 27, 1991 | [JP] | Japan | 3-33117 |

[51] Int. Cl.$^5$ .......... C12N 9/54; C12N 9/50; C12N 1/20; C12N 1/00
[52] U.S. Cl. .............. 435/71.2; 435/252.5; 435/219; 435/832; 435/221
[58] Field of Search ............. 435/221, 252.5, 219, 435/832, 71.2

[56] References Cited

U.S. PATENT DOCUMENTS

| 3,622,458 | 11/1971 | Murao | 435/222 |
| 4,480,037 | 10/1984 | Ichishima et al. | 435/222 |
| 4,511,490 | 4/1985 | Stanislowski et al. | 435/221 |
| 4,581,332 | 4/1986 | Soejima et al. | 435/220 |
| 4,764,470 | 8/1988 | Durham et al. | 435/221 |
| 4,771,003 | 9/1988 | Stellwag et al. | 435/221 |
| 4,797,362 | 1/1989 | Takeuchi et al. | 435/221 |
| 5,143,840 | 9/1993 | Rettenmaier et al. | 435/272 |

FOREIGN PATENT DOCUMENTS 247084  3/1988  Japan .

*Primary Examiner*—Irene Marx
*Assistant Examiner*—Jeffrey J. Sevigay
*Attorney, Agent, or Firm*—Oblon, Spivak, McClelland, Maier & Neustadt

[57] ABSTRACT

The present invention relates to a novel enzyme called alkaline proteinase K-16 that is characterized as having an optimum pH in an alkaline range, and stability in the presence of various surface active agents, such as sodium linear alkylbenzene sulfonate, sodium polyoxyethylene alkyl sulfate, sodium dodecyl sulfate, sodium α-olefin sulfonate, sodium alkyl sulfonate, and α-sulfofatty acid ester. The present invention further provides for the microorganism Bacillus sp. Ferm BP-3376, which is capable of producing the novel alkaline proteinase, and a process for producing the novel alkaline proteinase. Alkaline-proteinase K-16 of the present invention exhibits an excellent action against insoluble proteins and maintains sufficient activity over a wide temperature range and in the presence of surface active agents thus providing a use as an enzyme for detergents.

2 Claims, 4 Drawing Sheets

BACILLUS SP. FERM BP-3376 AND A METHOD FOR ITS USE TO PRODUCE AN ALKALINE PROTEINASE K-16

This is a division of application Ser. No. 07/816,243, filed on Jan. 3, 1992, now U.S. Pat. No. 5,296,367.

BACKGROUND OF THE INVENTION

1. Field of the Invention

The present invention relates to a novel alkaline proteinase K-16, a microorganism producing the alkaline proteinase, and a process for producing the alkaline proteinase. In particular, the present invention relates to a novel alkaline proteinase K-16 possessing excellent stability against surface active agents, as well as a microorganism and process for producing novel alkaline-proteinase.

2. Description of the Background Art

Conventionally, proteinases have been incorporated into detergents, and a number of alkaline proteinases are currently used as an enzyme for detergent. Typical examples of such alkaline proteinases are alkalase, savinase, espelase (a product of Novo Industries). A problem with many of these alkaline proteinases has been their inadequate stability in surfactant solutions.

There have been publications reporting alkaline proteinases which are stable against surface active agents, for example, Ya enzyme (Japanese Patent Laid-Open (kokai) No. 280278/1986). These enzymes, however, have their active region in a high temperature side, and therefore are not suitable for use as a detergent to be used around a room temperature, for example, as a detergent for washing clothes.

A proteinase, API-21 (Japanese Patent Publication (kokoku) No. 55118/1985) which is more active in a lower temperature range than conventional proteinases has been developed. Its stability in surfactant solutions, however, is still not satisfactory.

Development of an alkaline proteinase which is highly stable in surfactant solutions and which will function well in detergents has therefore been desired.

In view of this situation, the present inventors have carried out an extensive survey of soils in Japan in order to obtain microorganisms capable of producing alkaline proteinase, and, as a result, found that a microorganism belonging to genus Bacillus discovered from the soils in Haga-gun, Tochigi-ken, Japan, is capable of producing a novel alkaline proteinase which is stable in a detergent composition.

SUMMARY OF THE INVENTION

The present invention provides an alkaline proteinase, K-16, having the following enzymological characteristics:

(1) Action

Acts on various proteins under high alkaline conditions;

(2) Substrate specificity

Exhibits good activity on water-soluble protein, examples being casein, hemoglobin and FCS albumin; and water-insoluble proteins, for example, keratin and elastin;

(3) Optimum pH range

Optimum pH range of 11.0–12.3 when reacted at 40° C. using casein as a substrate;

(4) pH stability

Very stable in a pH range of 5.0–12.0 in the presence of $Ca^{2+}$ when stored in various buffer solutions at 25° C. for 2 days;

(5) Optimum temperature

Optimum temperature 55° C. when reacted at pH 10.0 using casein as a substrate;

(6) Heat stability

Maintains 90% or higher residual activity when treated at 50° C., pH 9.5 for 10 minutes.

(7) Molecular weight 28,000±1,000 measured by sodium dodecyl sulfate (SDS)-polyacrylamide gel electrophoresis;

(8) Isoelectric point 10.5 or higher;

(9) Effects of metal ions

The activity is inhibited by $Hg^{2+}$ and $Cu^{2+}$, and its heat stability is promoted by $Ca^{2+}$.

(10) Effects of inhibitors

The activity is not inhibited by ethylenediaminetetra-acetic acid, 4-chloromercuribenzoate and antipain, and the activity inhibited by diisopropylfluorophosphate, phenylmethanesulfonyl fluoride, and chymostatin ; and

(11) Effects of surface active agents

Very stable in the presence of high concentration of sodium linear alkylbenzene sulfonate, sodium polyoxyethylene alkyl sulfate, sodium dodecyl sulfate, sodium α-olefin sulfonate, sodium alkyl sulfonate, and α-sulfo-fatty acid ester.

This invention further provides a process for producing alkaline proteinase K-16 comprising culturing a microorganism belonging to the genus Bacillus which is capable of producing alkaline proteinase K-16 and collecting the enzyme from the culture broth.

A further object of the present invention is to provide a microorganism capable of producing alkaline proteinase K-16 belonging to the genus Bacillus, which is Bacillus sp. KSM-K16.

DETAILED DESCRIPTION OF THE INVENTION

Figure 1:
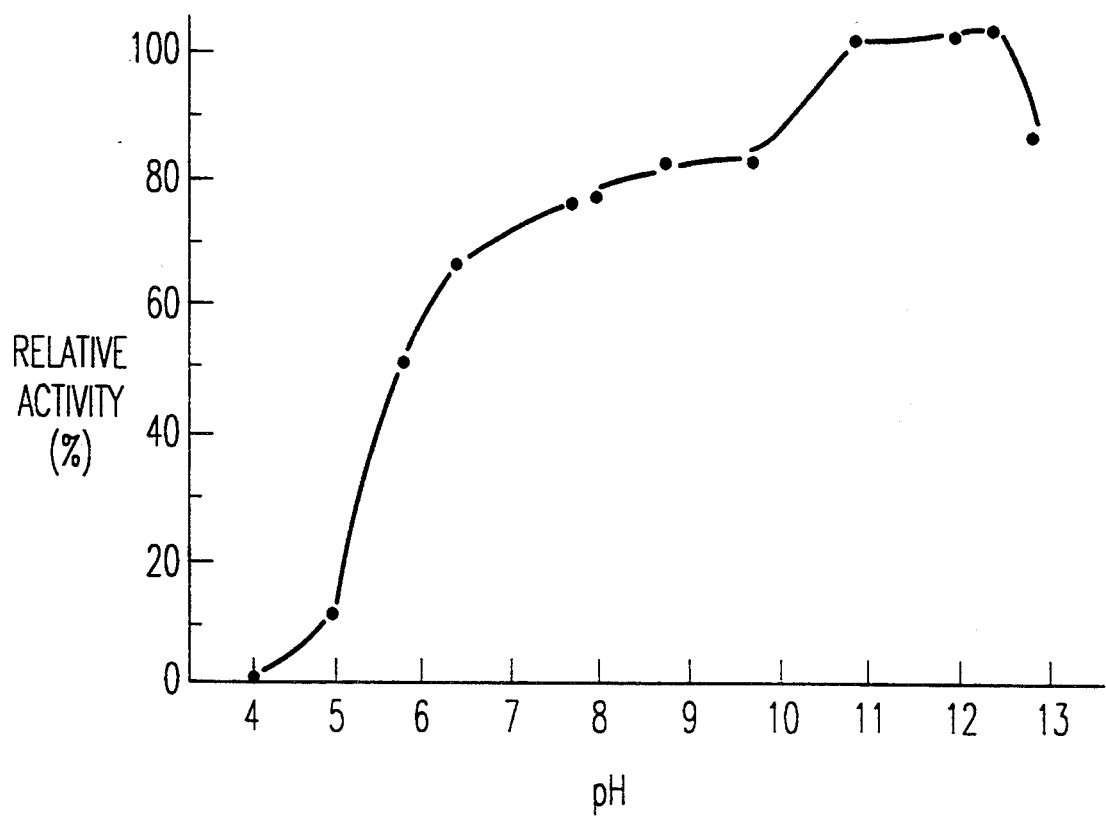
FIG. 1 represents the effects of pH on the activity of alkaline proteinase of the present invention.

The present invention relates to the enzyme, alkaline proteinase K-16, produced by the genus Bacillus which has the following taxonomic characteristics.

(A) Morphological characteristics (a) Shape and size of cells: rods, 0.8–1.0 μm×2.2–25 μm (b) Polymophism: None (c) Motility: Cells possess peritrichous flagella and motile.

(d) Spores (size, shape, site): 1.0–1.2 μm×1.4–2.2 μm, elliptical, central to subterminal; slightly swollen sporangium.

(e) Gram's staining: positive (f) Acid fastness: negative (g) Growth on nutrient agar plate: light yellow and transparent colony with a circular erose shape and a smooth surface.

(h) Growth on nutrient agar slant: Colony is light yellow and semitransparent with an irregular erose shape and a slightly rough surface.
(i) Culture in nutrient broth: Cells grow well, the broth is cloudy with no pellicle.
(j) Stab culturing in nutrient gelatin: Cells grow well; liquefaction of gelatin is accompanied.
(k) Litmus milk: Peptonization occurs, with no coagulation of milk. No color change occurs.

(B) Physiological characteristics
  (a) Nitrate reduction: Positive
  (b) Denitrification: Negative
  (c) MR test: Negative
  (d) V-P test: Positive
  (e) Production of indole: Negative
  (f) Production of hydrogen sulfide: Negative
  (g) Hydrolysis of starch: Positive
  (h) Utilization of citric acid: Positive
  (i) Utilization of inorganic nitrogen sources: Utilize sodium nitrate, but not ammonium salts
  (j) Pigment production: Negative
  (k) Urease: Negative
  (l) Oxidase: Positive
  (m) Catalase: Positive
  (n) Growth temperature range: Below 55° C.
  (o) Growth pH range: Can grow at pH 6.6–10.3
  (p) Behavior on oxygen: Aerobic
  (q) O–F test: Oxidation (O)
  (r) Resistance to sodium chloride: Can grow under 10% sodium chloride
  (s) Acid or gas production from sugar: Produces no gas from any sugars.

TABLE 1

| (Acid production from sugars) | |
|---|---|
| Sugars | Acid production |
| D-Ribose | + |
| L-Arabinose | + |
| D-Xylose | + |
| D-Fructose | + |
| D-Glucose | + |
| D-Mannose | + |
| D-Galactose | + |
| Maltose | + |
| Sucrose | + |
| Lactose | + |
| Trehalose | + |
| Starch | + |
| D-Sorbitol | + |
| Inositol | − |
| D-Mannitol | + |
| Glycerol | + |
| Dextrin | + |
| Raffinose | + |

Based on the above morphological and taxonomic characteristics, the microorganism of the present invention was examined referring to Bergey's Manual of Systematic Bacteriology (Williams & Wilkins Co., 1986) and was considered to belong to the genus *Bacillus subtilis*. However, there are differences between *Bacillus subtilis* and the microorganism of the present invention in that while the former cannot grow at pH 10, the latter can grow well at pH 10, and further that while *Bacillus subtilis* cannot grow at 55° C., the microorganism of the present invention can grow at 55° C.

From the above facts, notwithstanding the good reasons to speculate that the microorganism of the present invention belongs to *Bacillus subtilis*, it was judged to be another, novel microorganism due to several differences in their characteristics and also due to the differences from any other known microorganisms.

Thus, in another embodiment the present invention relates to the novel microorganism named Bacillus sp. KSM-K16 containing the properties described above, and has been deposited with the Fermentation Research Institute, Agency of Industrial Science and Technology as FERM BP-3376.

In a further embodiment, the present invention relates to a process for producing the alkaline proteinase K-16 which is extremely stable against surface active agents from this microorganism, Bacillus sp. KSM-K16, where the microorganism is inoculated and cultivated in a suitable medium according to a conventional manner.

Any media which are used for the cultivation of common microorganisms and in which the microorganism of the present invention can grow may be used for the cultivation. It is desirable to add a suitable amount of carbon and nitrogen sources which the microorganism can utilize in the medium.

There are no specific limitations as to the carbon and nitrogen sources. Enumerated as examples of nitrogen sources are corn gluten meal, soybean flour, corn steep liquor, casamino acid, yeast extract, pharmamedia, sardine meal, meat extract, peptone, hypro, ajipower, corn meal, soybean meal, coffee grounds, cotton seed grounds, cultivater, amiflex, ajipron, zest, ajix, and the like; and as carbon sources are arabinose, xylose, glucose, mannose, fructose, galactose, sucrose, maltose, lactose, sorbitol, mannitol, inositol, glycerol, soluble starch, inexpensive waste molasses, invert sugars, as well as utilizable organic acids such as acetic acid and the like. In addition to these carbon and nitrogen sources, phosphoric acid, inorganic salts of ions such as $Mg^{2+}$, $Ca^{2+}$, $Mn^{2+}$, $Zn^{2+}$, $Co^{2+}$, $Na^+$, $K^+$, for example, as well as trace amounts of other organic or inorganic nutrients, may be added as required.

Collection and purification of target alkaline proteinase K-16 from the culture broth thus prepared can be performed according to conventional methods applicable to the collection and purification of common enzymes.

Specifically, cells are separated from the culture broth by centrifugation or filtration, for example, and alkaline proteinase K-16 can be separated and concentrated from the cells and the filtrate by a conventional separation means such as salting out, isoelectric precipitation, solvent precipitation, examples being precipitation from methanol, ethanol, isopropyl alcohol, acetone, or the like; ultrafiltration, for example, using Diaflow membrane YC (trademark, a product of Amicon Co.), and the like. It is possible to produce lyophilized powder of the enzyme by collecting the enzyme by salting out using, for example, ammonium sulfate (30–70% saturation fraction), or by solvent precipitation from, for example, 75% ethanol, followed by filtration or centrifugation, and desalting. A conventional method such as dialysis or gel filtration using Sephadex G-25 (trademark, a product of Pharmacia) can be employed for the desalting.

Although it is possible to use the crude enzyme liquid thus obtained as is, the enzyme can also be served after purification and crystallization, as required. Such purification can be carried out by a suitable combination of fractionation means, such as, for example, adsorption chromatography, e.g., hydroxyapatite chromatography, ion-exchange chromatography, e.g., DEAE- Sephadex, DEAE-Cellulose, or CM-Bio-Gel; or gel filtration chromatography, e.g., Sephadex or Bio-Gel.

Alkaline proteinase K-16 thus obtained has the following enzymological characteristics. Enzymatic activities discussed herein were measured by the following methods.

A 1% solution of casein in 50 mM borate-NaOH buffer (pH 10.0, 1 ml) was mixed with 0.1 ml of an enzyme solution and incubated at 40° C. for 10 minutes. After the addition of a reaction termination solution (0.123M trichloroacetic acid-0.246M sodium acetate-0.369M acetic acid), the mixture was allowed to stand at 30° C. for 20 minutes and filtered by No. 2 filter (made by Wattman Co.). Protein decomposition products in filtrate was measured by the modified Folin-Lowry method. One unit (P.U.) of enzymatic activity was defined as the amount of enzyme that released acid soluble amino acid or peptid equivalent to 1 mmol of tyrosine per minute under the above reaction conditions.

(1) Action

Acts on various proteins under high alkaline conditions.

(2) Substrate specificity

The specificity toward various substrates of alkaline proteinase K-16 and commercial enzymes were compared. Substrates used were casein, urea-denatured hemoglobin, animal hair keratin, and elastin. Degradation activities of the enzyme on these substances were measured. Each substrate was added to 50 mM borate-NaOH buffer (pH 10.0) to make its concentration 1% (2.2% for urea-denatured hemoglobin), and to the solution was added each enzyme solution in an amount of $0.5 \times 10^{-4}$ P.U. ($3.5 \times 10^{-4}$ P.U. for elastin). The mixture was incubated at 40° C. for 10 minutes. The activity of each enzyme toward each substrate is shown in Table 2, wherein alkaline proteinase K-16 is taken as 100.

TABLE 2

| | Casein | Urea-denatured hemoglobin | Animal hair Keratin | elastin |
| --- | --- | --- | --- | --- |
| K-16 | 100 | 100 | 100 | 100 |
| Commercial enzyme A | 100 | 108 | 100 | 77 |
| Commercial enzyme b | 100 | 100 | 103 | 76 |

As shown in the above Table, alkaline proteinase K-16 of the present invention exhibited better degradation activity, particularly toward elastin, than commercial enzymes A and B which are widely used as enzymes for detergents due to their excellent capability of decomposing both water-soluble and water-insoluble proteins.

(3) Optimum pH range

Casein was added to various buffer solutions (50 mM) to a final concentration of 0.91%, and then $5.2 \times 10^{-5}$ P.U. of alkaline proteinase K-16 was added to the solution. The mixture was incubated at 40° C. for 10 minutes to measure the enzyme activity. Activities of the enzyme at various pHs relative to optimum pH (100) are shown in FIG. 1, which indicates that the optimum pH range of alkaline proteinase K-16 of the present invention is 11.0-12.3. The buffer solutions used in the measurement and their pHs are as follows.

| Acetate buffer | pH 3.9-5.7 |
| --- | --- |
| Phosphate buffer | pH 6.6-8.3 |
| Carbonate buffer | pH 9.2-10.9 |
| Phosphate-NaOH buffer | pH 10.9-12.7 |
| KCl—NaOH buffer | pH 10.9-12.6 |

Figure 2:
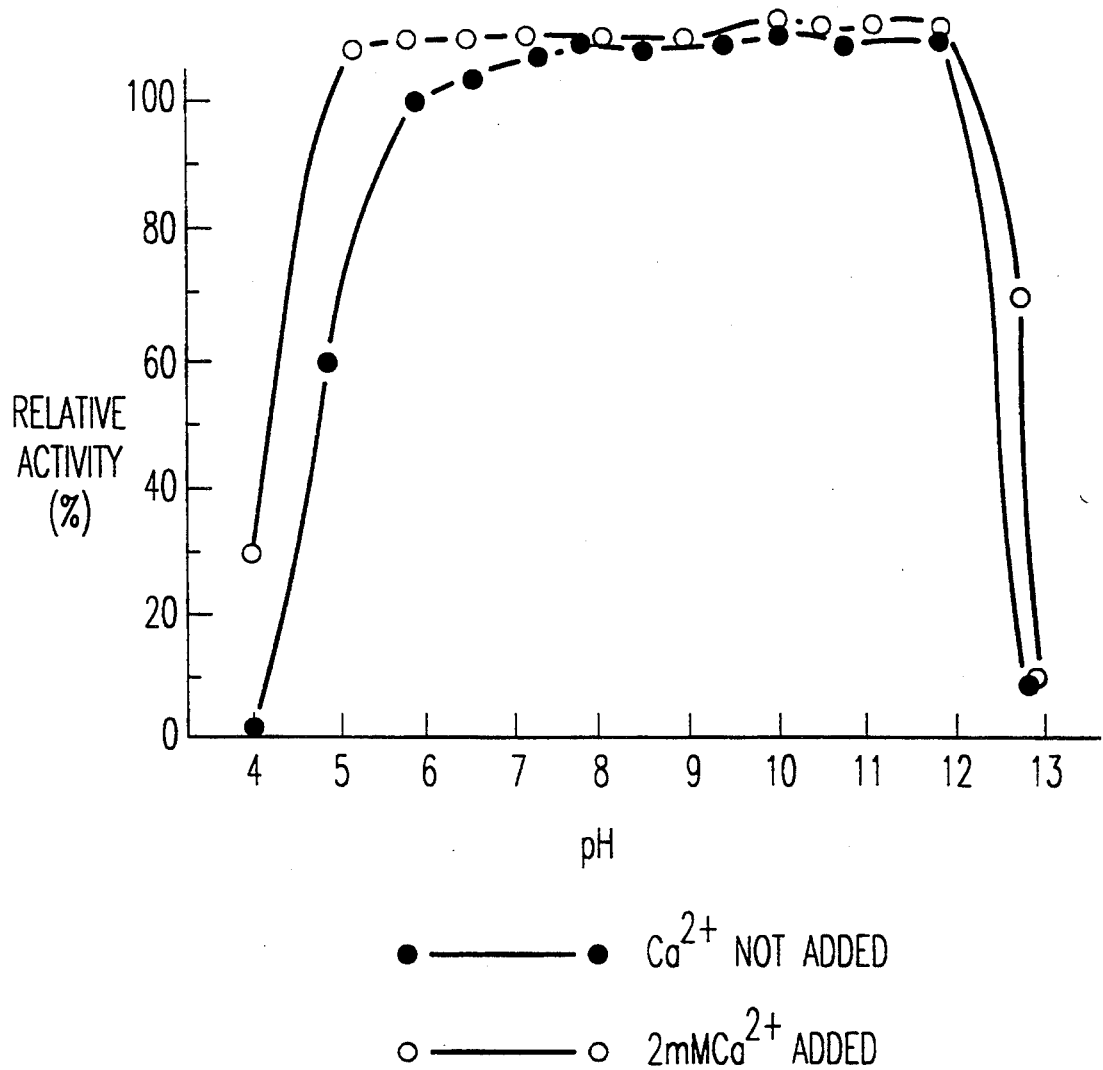
FIG. 2 shows the effects of pH on the stability of alkaline proteinase of the present invention.

(4) pH stability $7.9 \times 10^{-3}$ P.U. of alkaline proteinase K-16 was added to the same buffer solutions (20 mM) as used in (3) above. The solution was allowed to stand at 25° C. for 2 days and diluted with 50 mM borate-NaOH buffer solution (pH 10.0) to a volume of 40 folds to measure the enzyme activity. Activities of the enzyme relative to the activity before the treatment (100%) were determined and the results are shown in FIG. 2, which shows the stable pH range of alkaline proteinase K-16 is 6.0-12.0 in the absence of $Ca^{2+}$ and 5.0-12.0 in 2 mM $Ca^{2+}$.

Figure 3:
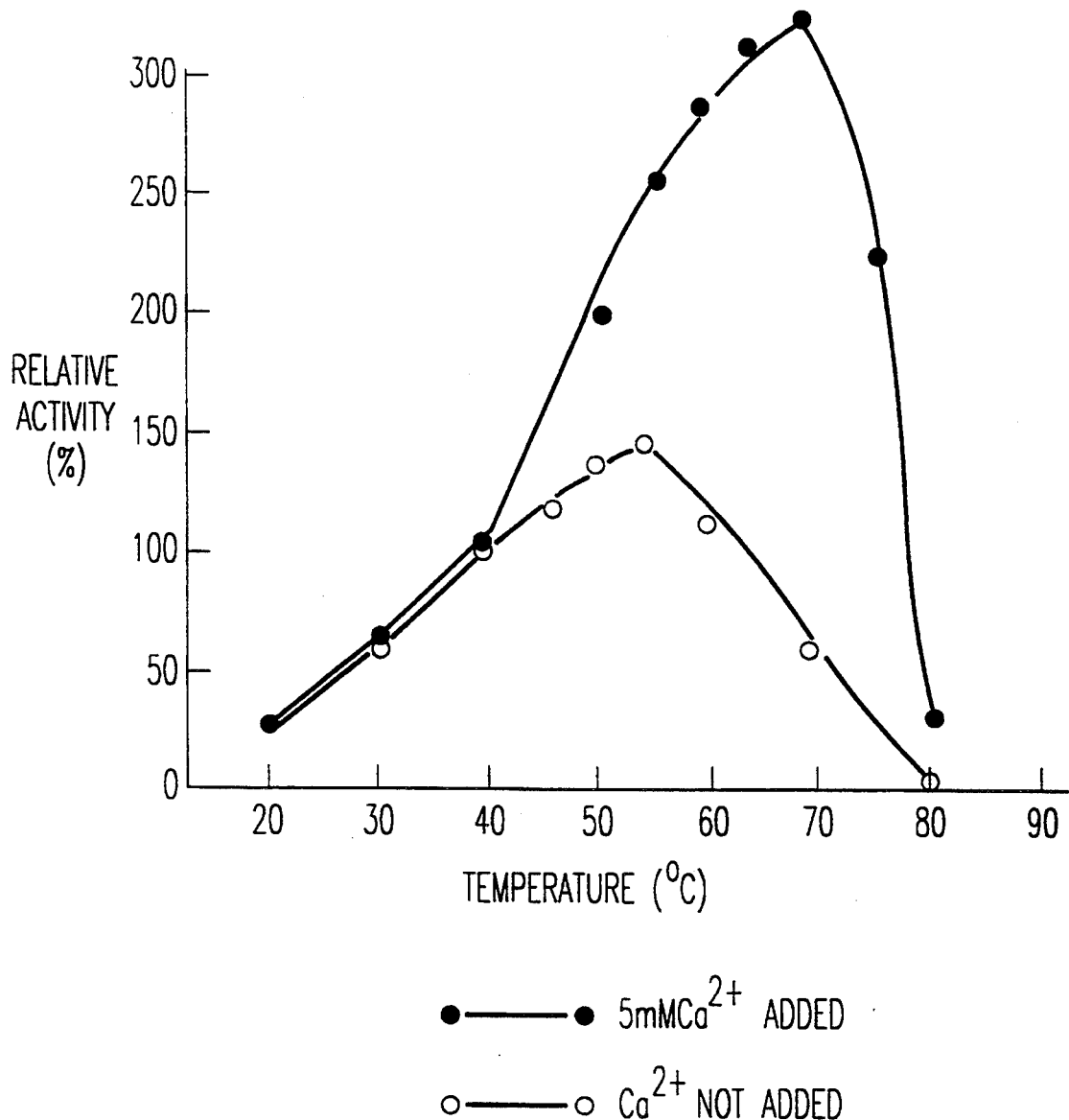
FIG. 3 shows the effects of temperature on the activity of alkaline proteinase of the present invention.

(5) Optimum temperature $3.1 \times 10^{-5}$ P.U. of alkaline proteinase K-16 was added to 50 mM borate-NaOH buffer solution (pH 10.0) which contained 0.91% of casein and incubated at various temperatures for 10 minutes. Activities of the enzyme at each temperature relative to the activity at 40° C. (100%) were determined and the results are shown in FIG. 3, which shows the optimum temperature range of alkaline proteinase K-16 is 55° C. in the absence of $Ca^{2+}$ and 70° C. in the presence of 5 mM $Ca^{2+}$.

Figure 4:
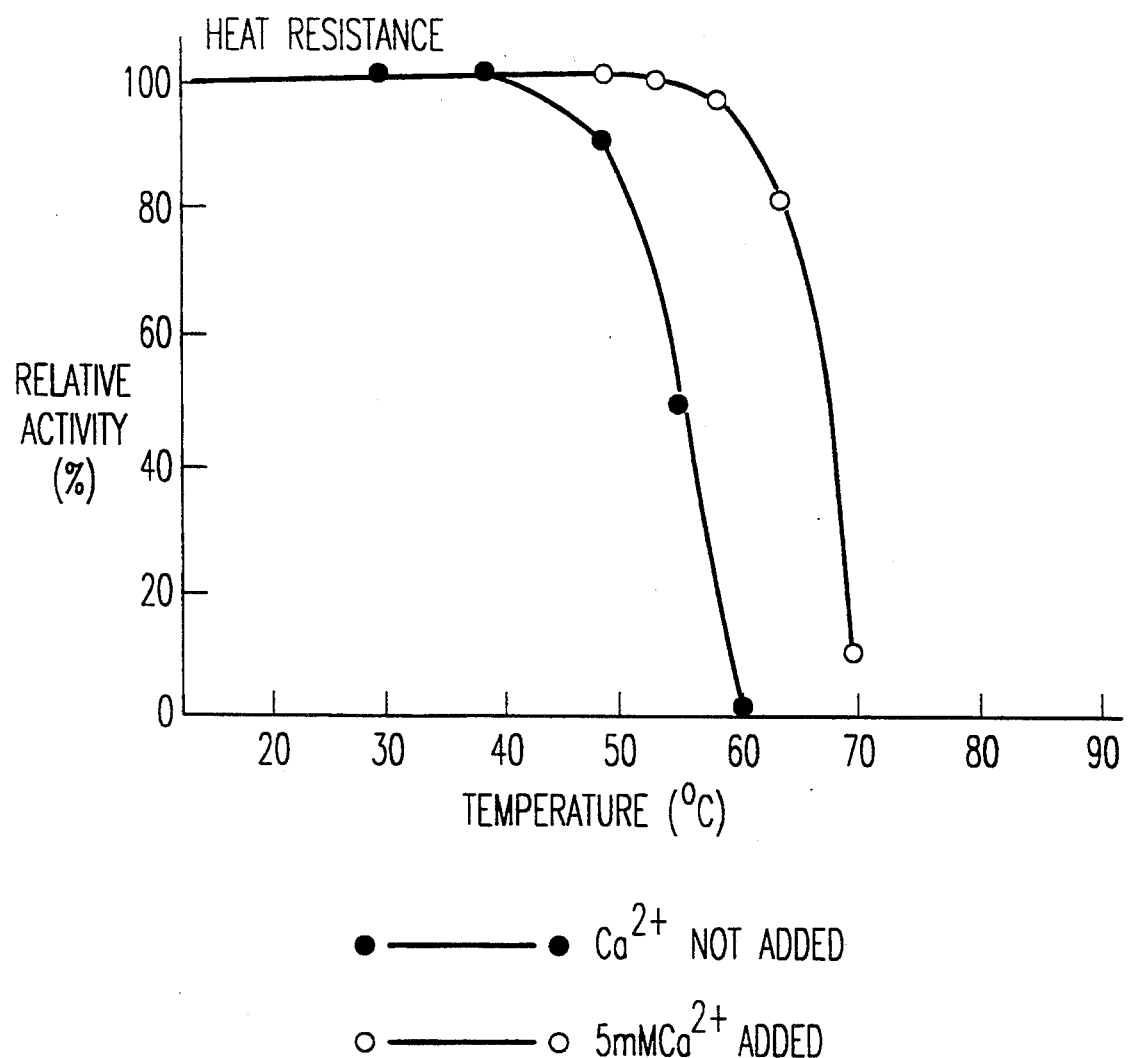
FIG. 4 shows the effects of temperature on the stability of alkaline proteinase of the present invention.

(6) Heat stability $1.6 \times 10^{-3}$ P.U. of alkaline proteinase K-16 was added to 20 mM borate-NaOH buffer (pH 9.5) and heated at various temperatures for 10 minutes. After cooling, the solution was diluted to a volume of 5 folds with 50 mM borate-NaOH buffer (pH 10.0) and the enzyme activities were measured using 0.91% casein as a substrate. Activities of the enzyme at each temperature relative to the activity before the treatment (100) were determined and the results are shown in FIG. 4, which shows alkaline proteinase K-16 maintained 90% or more of the activity up to 50° C. in the absence of $Ca^{2+}$ and up to 60° C. in the presence of 5 mM $Ca^{2+}$.

(7) Molecular weight

Molecular weight of alkaline proteinase K-16 was measured by the sodium dodecyl sulfate (SDS)-polyacrylamide gel electrophoresis. As molecular weight (M.W.) markers, a low M.W. marker kit (Bio-Rad); phosphorylase b (M.W. 97,400), FCS albumin (M.W. 66,200), egg white albumin (M.W. 42,700), carbonic anhydrase (M.W. 31,000), soybean trypsin inhibitor (M.W. 21,500), lysozyme (M.W. 14,400) was used. The M.W. of alkaline proteinase K-16 of the present invention was found to be 28,000±1,000 by the measurement by this method.

(8) Isoelectric point

Isoelectric point of alkaline proteinase K-16 was examined by the electrofocusing method using Servalyt 9-11 as an amphoteric carrier for the column. The isoelectric point of alkaline proteinase K-16 of the present invention was determined by this method to be pH 10.5 or higher.

(9) Effects of metal ions

Effects of various metals on alkaline proteinase K-16 were examined. Various metal ions were added to 20 mM borate-NaOH buffer (pH 9.5) to a concentration of 1 mM $3.9 \times 10^{-3}$ P.U. of alkaline proteinase K-16 was added to the buffer solutions and allowed to stand at 30° C. for 20 minutes. The resulting solution was diluted with 50 mM borate-NaOH buffer (pH 10.0) to a volume of 5 folds to measure the residual enzyme activity. Residual activities were expressed by the relative activity to the enzyme activity without the addition of a metal ion. The results are shown in Table 3, which shows the activity of alkaline proteinase K-16 of the present invention is inhibited by $Hg^{2+}$ and $Cu^{2+}$.

Also, from the results of (5) and (6) above $Ca^{2+}$ promotes the heat stability of the enzyme.

TABLE 3

| Metal salt (1 mM) | Residual Activity (%) |
| --- | --- |
| Not added | 100 |
| $ZnCl_2$ | 106 |
| $AgNO_3$ | 86 |
| $CaCl_2$ | 103 |
| $NiCl_2$ | 103 |
| $CoCl_2$ | 103 |
| $PbCl_2$ | 100 |
| $HgCl_2$ | 46 |
| $CuSO_4$ | 73 |

(10) Effects of inhibitors

Effects of common enzyme inhibitors on alkaline proteinase K-16 were examined. The tested inhibitors were added to 10 mM phosphate buffer (pH 7.0) to a prescribed concentration. $7.9 \times 10^{-3}$ P.U. of alkaline proteinase K-16 was then added to the buffer solutions and allowed to stand at 30° C. for 20 minutes. The resulting solution was diluted with deionized water to a volume of 20 folds to measure the residual enzyme activity. Residual activities was expressed by the relative activity to the enzyme activity without the addition of a inhibitor. The results are shown in Table 4, which shows the activity of alkaline proteinase K-16 of the present invention is inhibited by diisopropylfluorophosphate (DFP), phenylmethanesulfonyl fluoride (PMSF), and chymostatin, which are serine protease inhibitors, demonstrating that it is an enzyme with a serine residue as its active center.

TABLE 4

| Inhibitor | Concentration | Residual activity (%) |
| --- | --- | --- |
| Not added | — | 100 |
| EDTA | 5 mM | 107 |
| CMB | 1 mM | 100 |
| DFP | 1 mM | 3.8 |
| PMSF | 1 mM | 1.5 |
| Antipain | 0.01% | 108 |
| chymostatin | 0.01% | 34 |

EDTA: Ethylenediaminetetraacetic acid
CMB: 4-chloromercuribenzoate
DFP: Diisopropylfluorophosphate
PMSF: Phenylmethanesulfonyl fluoride

(11) Effects of surface active agents

Various surface active agents were dissolved into 0.1M Tris-HCl buffer (pH 9.0; contains 10% of ethanol), and $6.6 \times 10^{-2}$ P.U. of alkaline protease K-16 was added to the solution. The mixture was allowed to stand at 40° C. for 4 hours. The resulting solution was diluted with 50 mM borate-NaOH buffer solution (pH 10.0) to a volume of 20 folds to measure the residual enzyme activity. Residual activities were expressed as percentages of the original activity (no treatment), taken as 100%. The results are shown in Table 5, which shows that the activity of alkaline proteinase K-16 of the present invention remains stable in the presence of various surface active agents at high concentrations (1–10%).

TABLE 5

| | K-16 | Commercial Enzyme B | Commercial Enzyme C |
| --- | --- | --- | --- |
| Sodium linear alkyl-benzene sulfonate*1 (1%) | 65(%) | 48(%) | 46(%) |
| Sodium polyoxyethylene alkyl sulfate*2 (1%) | 100 | 97 | 52 |
| Sodium dodecyl sulfate*3 (10%) | 58 | 0 | 48 |
| Sodium α-olefin sulfonate*4 (1%) | 100 | 82 | 61 |
| Sodium alkyl sulfonate*5 (10%) | 81 | 23 | 72 |
| α-Sulfo-fatty acid ester*6 (1%) | 100 | 86 | 75 |
| Softanol 70H*7 (1%) (a product Nippon Shokubai) | 100 | 84 | 90 |

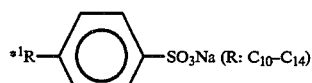

*2R—$CH_2O(C_2H_4O)_nSO_3Na$ (R: $C_9$–$C_{17}$, n = 1–5)
*3R—$CH_2OSO_3Na$ (R: $C_9$–$C_{17}$, But the $C_{12}$ is principal)
*4R—$CH=CH(CH_2)_nSO_3Na$ (R: $C_7$–$C_{15}$, n = 0.1–5)

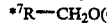

*7R—$CH_2O(C_2H_4O)_nH$ (R: $C_8$–$C_{17}$, n = 5–15)

As illustrated above, alkaline proteinase K-16 of the present invention exhibits a superior action on insoluble proteins, maintains its activity in a wide temperature range, and is very stable in surface active agents. Thus, alkaline proteinase K-16 is useful as an enzyme that may be added to detergent composition.

Other features of the invention will become apparent in the course of the following description of the exemplary embodiments which are given for illustration of the invention and are not intended to be limiting thereof.

EXAMPLES

Example 1

Separation and collection of the proteinase-producing microorganism (1) About 1 g of a soil sample was suspended in 10 ml of sterilized physiological saline and heat-treated at 80° C. for minutes. A supernatant of the heat-treated suspension (0.1 ml) was spread on a keratin agar medium and cultivated at 30° C. for 2 days. The composition of the keratin agar medium was as follows.

| | |
| --- | --- |
| Glucose | 1% |
| Yeast extract | 0.2% |
| Animal hair keratin | 1% |
| Carboxymethyl cellulose | 1% |
| Potassium (I) phosphate | 0.1% |
| $MgSO_4 \cdot 7H_2O$ | 0.02% |
| Agar | 1.5% |

(2) To the above keratin agar medium was added 1% of sterilized 10% sodium carbonate solution to adjust the pH 10.5. After the cultivation, colonies that formed a clear zone around their margins were picked up and repeatedly purified on the same agar medium, thus obtaining a pure proteinase producing microorganism.

(3) Cells obtained in (2) above were inoculated into the liquid medium with the following composition and cultured at 30° C. for 2 days, with shaking, on a reciprocal shaker.

| | | |
|---|---|---|
| Glucose | 2.0% | |
| Polypepton S | 1.0% | |
| Yeast extract | 0.05% | |
| Potassium (I) phosphate | 0.1% | |
| $MgSO_4 \cdot 7H_2O$ | 0.02% | |
| Sodium carbonate | 1.0% | |
| (separately sterilized) | (pH 10.5) | |

After the cultivation, the culture broth was centrifuged (3,000 rpm, 10 minutes) to remove cells to obtain a supernatant as an enzyme solution.

(4) Crude enzyme samples were prepared by lyophilizing the enzyme solutions obtained in (3) above. The storage stability of the enzymes at 40° C. in a commercial detergent was evaluated. A strain which can produce the most stable enzyme was thus obtained as Bacillus sp. KSM-K16.

Example 2

Cultivation of cells and purification of alkaline proteinase K-16

(1) The alkalophilic Bacillus sp. KSM-K16 obtained in Example 1 was inoculated into the following liquid medium (3.0 l) and cultured at 30° C. for 2 days, with shaking, to produce alkaline proteinase K-16.

| | |
|---|---|
| Glucose | 2.0% |
| Fish meat extract | 1.0% |
| Soybean flour | 1.0% |
| $MgSO_4 \cdot 7H_2O$ | 0.02% |
| Potassium (I) phosphate | 0.1% |
| | (pH 10.5) |

(2) After the cultivation, 3.0 l of the culture broth was centrifuged (10,000 rpm, 5 minutes) to remove cells. The supernatant thus obtained was lyophilized and 2 g of the dried powder was dissolved in 10 ml of deionized water to produce a crude enzyme solution. The solution was dialyzed overnight against 10 mM Tris-HCl buffer (contains 2 mM $Ca^{2+}$, pH 7.5) and 26 ml of retentate (activity, 3.15 P.U./ml; specific activity, 1.97 P.U./mg protein) was obtained. This retentate was subjected to a column packed with CM-52 cellulose which had been equilibrated with 10 mM Tris-HCl buffer (contains 2 mM $Ca^{2+}$, pH 7.5). After washing the column with the equilibrating buffer, alkaline proteinase K-16 was eluted with a gradient of 0 to 0.15M sodium chloride in the same buffer. The active fractions collected was 15 ml, and its activity was found to be 1.12 P.U./ml and the specific activity 5.75 P.U./mg protein. The active fraction was dialyzed overnight against 50 mM Tris-HCl buffer (contains 10 mM $Ca^{2+}$ and 0.2M NaCl, pH 8.0), concentrated by ultrafiltration (5000-M.W. cut off; Amicon Co.), applied to a column of Sephadex G-50 (Pharmacia) which had been equilibrated with 50 mM Tris-HCl buffer (contains 10 mM $Ca^{2+}$ and 0.2M NaCl, pH 8.0), and elution was done with the same buffer. The active fractions collected was 11.5 ml, and its activity was 0.9 P.U./ml and the specific activity was 6.03 P.U./mg protein.

The solution was dialyzed overnight against deionized water to obtain a retentate with an activity of 0.56 P.U./ml and a specific activity of 5.60 P.U./mg protein.

All publications mentioned hereinabove are hereby incorporated by reference.

While the foregoing invention has been described in some detail for purposes of clarity and understanding, it will be appreciated by one skilled in the art from reading of this disclosure that various changes in form and detail can be made without departing from the true scope of the invention.

What is claimed is:

1. A process for producing alkaline proteinase K-16 comprising:
   (i) culturing the microorganism Bacillus sp. FERM BP-3376 in a culture broth; and
   (ii) collecting said alkaline proteinase K-16 from the culture broth.

2. A biologically pure culture of the microorganism Bacillus sp. FERM BP-3376.

* * * * *